US010633677B2

United States Patent
Shen et al.

(10) Patent No.: US 10,633,677 B2
(45) Date of Patent: Apr. 28, 2020

(54) BUTANOL EXPRESSION CASSETTE, RECOMBINANT PLASMID AND BUTANOL PRODUCTION RELATED GENE EXPRESSION METHOD

(71) Applicants: National Tsing Hua University, Hsinchu (TW); Chang Chun Plastics Co., Ltd., Taipei (TW); Chang Chun Petrochemical Co., Ltd., Taipei (TW)

(72) Inventors: Roa-Pu Shen, Hsinchu (TW); Rex C. Wen, Hsinchu (TW)

(73) Assignees: National Tsing Hua University, Hsinchu (TW); Chang Chun Plastics Co., Ltd., Taipei (TW); Chang Chun Petrochemical Co., Ltd., Taipei (TW)

( * ) Notice: Subject to any disclaimer, the term of this patent is extended or adjusted under 35 U.S.C. 154(b) by 27 days.

(21) Appl. No.: 15/598,316

(22) Filed: May 18, 2017

(65) Prior Publication Data

US 2018/0179556 A1 Jun. 28, 2018

(30) Foreign Application Priority Data

Dec. 27, 2016 (TW) .............................. 105143363 A (51) Int. Cl.
| C12P 7/16 | (2006.01) |
| C12N 9/04 | (2006.01) |
| C12N 9/02 | (2006.01) |
| C12N 9/12 | (2006.01) |
| C12N 9/10 | (2006.01) |
| C12N 15/70 | (2006.01) |
| C12N 15/52 | (2006.01) |

(52) U.S. Cl.
CPC .............. *C12P 7/16* (2013.01); *C12N 9/001* (2013.01); *C12N 9/0006* (2013.01); *C12N 9/0008* (2013.01); *C12N 9/1029* (2013.01); *C12N 9/1217* (2013.01); *C12N 15/52* (2013.01); *C12N 15/70* (2013.01); *C12Y 101/01001* (2013.01); *C12Y 101/0103* (2013.01); *C12Y 101/01027* (2013.01); *C12Y 101/01322* (2015.07); *C12Y 102/01004* (2013.01); *C12Y 103/01086* (2013.01); *C12Y 103/05004* (2013.01); *C12Y 203/01009* (2013.01); *C12Y 207/02001* (2013.01); *C12N 2800/101* (2013.01)

(58) Field of Classification Search
None
See application file for complete search history.

(56) References Cited

U.S. PATENT DOCUMENTS

| 2009/0155869 A1 | 6/2009 | Buelter et al. |
| 2010/0151544 A1 | 6/2010 | Papoutsakis et al. |
| 2015/0299736 A1 | 10/2015 | Yazdani et al. |

FOREIGN PATENT DOCUMENTS

| CN | 101058799 | 10/2007 |
| TW | I401317 | 7/2013 |
| TW | I512105 | 12/2015 |
| TW | I535844 | 6/2016 |
| WO | 2012099934 | 7/2012 |
| WO | WO 2012/099934 A2 * | 7/2012 |
| WO | WO 2014/055649 A1 * | 10/2014 |

OTHER PUBLICATIONS

Rex C. Wen, et al., "Self-regulated 1-butanol production in *Escherichia coli* based on the endogenous fermentative control," Biotechnol Biofuels, vol. 9, No. 267, Dec. 19, 2016, pp. 1-15.
Claire R. Shen, et al., "Driving Forces Enable High-Titer Anaerobic 1-Butanol Synthesis in *Escherichia coli*," Applied and Environmental Microbiology, May 2011, pp. 2905-2915.
Ethan I. Lan, et al., "Metabolic engineering of cyanobacteria for 1-butanol production from carbon dioxide," Metabolic Engineering, vol. 13, May 2011, pp. 353-363.
"Office Action of Taiwan Counterpart Application," dated Oct. 17, 2017, p. 1-p. 7, in which the listed references were cited.

* cited by examiner

*Primary Examiner* — Iqbal H Chowdhury
(74) *Attorney, Agent, or Firm* — JCIPRNET (57) ABSTRACT

A butanol expression cassette includes a butanol production related genes and a fermentation regulatory element. The fermentation regulatory element controls the expression of the butanol production related gene and locates upstream of the butanol production related gene. The fermentation regulatory element includes a promoter, a ribosome binding site and a transcription factor binding site of a fermentation gene. A fermentation in which the fermentation regulatory element involves includes an acetic acid fermentation, an alcohol fermentation, a succinic acid fermentation or a lactic acid fermentation, the butanol production related gene is not the fermentation gene or a gene of an upstream product of the fermentation in which the fermentation gene involves. The present invention provides a recombinant plasmid formed by cloning the butanol expression cassettes in the expression vector. The present invention also provides a butanol production related gene expression method to express butanol production related gene by using recombinant plasmid.

9 Claims, 5 Drawing Sheets

Specification includes a Sequence Listing.

BUTANOL EXPRESSION CASSETTE, RECOMBINANT PLASMID AND BUTANOL PRODUCTION RELATED GENE EXPRESSION METHOD

CROSS-REFERENCE TO RELATED APPLICATION

This application claims the priority benefit of Taiwan application serial no. 105143363, filed on Dec. 27, 2016. The entirety of the above-mentioned patent application is hereby incorporated by reference herein and made a part of this specification.

BACKGROUND OF THE INVENTION

1. Field of the Invention

The invention is related to a butanol expression cassette, a recombinant plasmid and a butanol production related gene expression method, and particularly related to a butanol expression cassette, a recombinant plasmid and a butanol production related gene expression method able to achieve self-regulating.

2. Description of Related Art

In recent years, the technology of expressing the exogenous gene by gene engineering has been widely applied in the related fields such as medicine, agriculture, animal husbandry, food industry or chemical industry. In the conventional gene engineering technology, the exogenous gene is cloned in the expression vector and the recombinant plasmid is constructed, then the recombinant plasmid is transformed to the host cell. Then, the host cell is induced to significantly express the exogenous gene by the addition of the inducer. Among the above, the host cell used to express the exogenous gene is usually microbial or mammalian cells, etc.

Generally, specific genes (such as the antibiotic resistance genes) are contained in the recombinant plasmid, therefore, by the addition of antibiotics or inducers, the successfully transformed host cell can keep the recombinant plasmid therein. However, the addition of antibiotics or inducers causes the inconvenience or increased cost of the product manufacturing process. Therefore, the production platform without the addition of inducer or antibiotics is a problem to be solved.

SUMMARY OF THE INVENTION

The present invention provides a butanol expression cassette, having a fermentation regulatory element able to achieve self-regulating.

The present invention provides a recombinant plasmid, configured to express the butanol production related gene.

The present invention provides a butanol production related gene expression method, able to express the butanol production related gene under a fermentation condition.

The butanol expression cassette of the invention includes a butanol production related genes and a fermentation regulatory element. The fermentation regulatory element is configured to control the expression of the butanol production related gene and locates upstream of the butanol production related gene. The fermentation regulatory element includes a promoter, a ribosome binding site and a transcription factor binding site of a fermentation gene. Among the above, the fermentation in which the fermentation regulatory element involves includes an acetic acid fermentation, an alcohol fermentation, a succinic acid fermentation or a lactic acid fermentation, the butanol production related gene is not the fermentation gene or the gene of the upstream product of the fermentation in which the fermentation gene involves.

In an embodiment of the invention, the fermentation gene includes an ackA gene, an adhE gene, an frdA gene or an ldhA gene.

In an embodiment of the invention, when the fermentation gene is the ackA gene, the fermentation regulatory element has a sequence of SEQ ID NO: 1.

In an embodiment of the invention, when the fermentation gene is the adhE gene, the fermentation regulatory element has a sequence of SEQ ID NO:2.

In an embodiment of the invention, when the fermentation gene is the frdA gene, the fermentation regulatory element has a sequence of SEQ ID NO:3.

In an embodiment of the invention, when the fermentation gene is the ldhA gene, the fermentation regulatory element has a sequence of SEQ ID NO:4.

In an embodiment of the invention, the butanol production related gene includes an atoB gene, an adhE2 gene, a crt gene, an hbd gene, a ter gene or an fdh gene.

The present invention provides a recombinant plasmid, configured to express the butanol production related gene. The recombinant plasmid includes an expression vector and the above-mentioned butanol expression cassette cloned in the expression vector.

In an embodiment of the invention, the expression vector includes an expression vector containing a ColE1 replication origin, an expression vector containing a Cola replication origin or an expression vector containing a pSC101 replication origin.

The present invention also provides a butanol production related gene expression method, including the following steps. First, the above-mentioned recombinant plasmid is transformed in a host cell, wherein the fermentation gene or the gene of the upstream product of the fermentation in which the fermentation gene involves have been eliminated from the host cell. Then, the host cell is cultured under a fermentation condition, and the recombinant plasmid is induced to express the butanol production related gene.

In an embodiment of the invention, the host cell can't grow under an anaerobic environment.

In an embodiment of the invention, after the recombinant plasmid containing the butanol-related gene is transformed in the host cell unable to grow under an anaerobic environment, the host cell having the recombinant plasmid expresses the butanol-related gene, and can be grown and produced the butanol under an anaerobic environment.

In an embodiment of the invention, the method of inducing the recombinant plasmid is cultured under a microaerobic environment or an anaerobic environment.

In an embodiment of the invention, the step of culturing the host cell includes culturing the host cell to an early phase of a growth log phase or a late phase of the growth log phase under an aerobic environment, and transferring to an anaerobic environment for continuous culturing.

In an embodiment of the invention, in the anaerobic environment, a pH value is adjusted to 6.8 to 7.2 every 8 to 24 hours, and a glucose concentration is adjusted to being equal to or higher than 20 g/L.

In an embodiment of the invention, the host cell includes an *Escherichia coli*.

In an embodiment of the invention, a gene eliminated from the host cell includes a pta gene, an adhE gene, an frdBC gene, an ldhA gene or a combination thereof.

Based on the above, the butanol expression cassette, the recombinant plasmid and the butanol production related gene expression method include the fermentation regulatory element of the host cell itself, so the butanol production related gene can be expressed in a self-regulating manner without the use of inducers or antibiotics. Therefore, the embodiment of the invention is beneficial to increasing the production amount of butanol production related gene and reducing the production cost of the butanol production related gene.

To make the above features and advantages of the invention more comprehensible, several embodiments accompanied with drawings are described in detail as follows.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

In the following, the embodiments of the invention are described. However, the embodiments are illustrative only, and the disclosure of the invention is not limited thereto.

In an embodiment of the invention, a butanol expression cassette is provided, including a butanol production related gene and a fermentation regulatory element. The fermentation regulatory element is configured to control the expression of the butanol production related gene and locates upstream of the butanol production related gene. The fermentation regulatory elements (FRE) is the fermentation regulatory element of the gene involved in the fermentation (referred to as the fermentation gene), which includes a promoter, a ribosome binding site and a transcription factor binding site, as shown in FIG. 1A.

In an embodiment, the fermentation gene is the gene involved in the oxidation of NADH into NAD or the production of ATP. Specifically, the fermentation in which the fermentation gene involves includes an acetic acid fermentation, an alcohol fermentation, a succinic acid fermentation or a lactic acid fermentation.

Figure 1A:
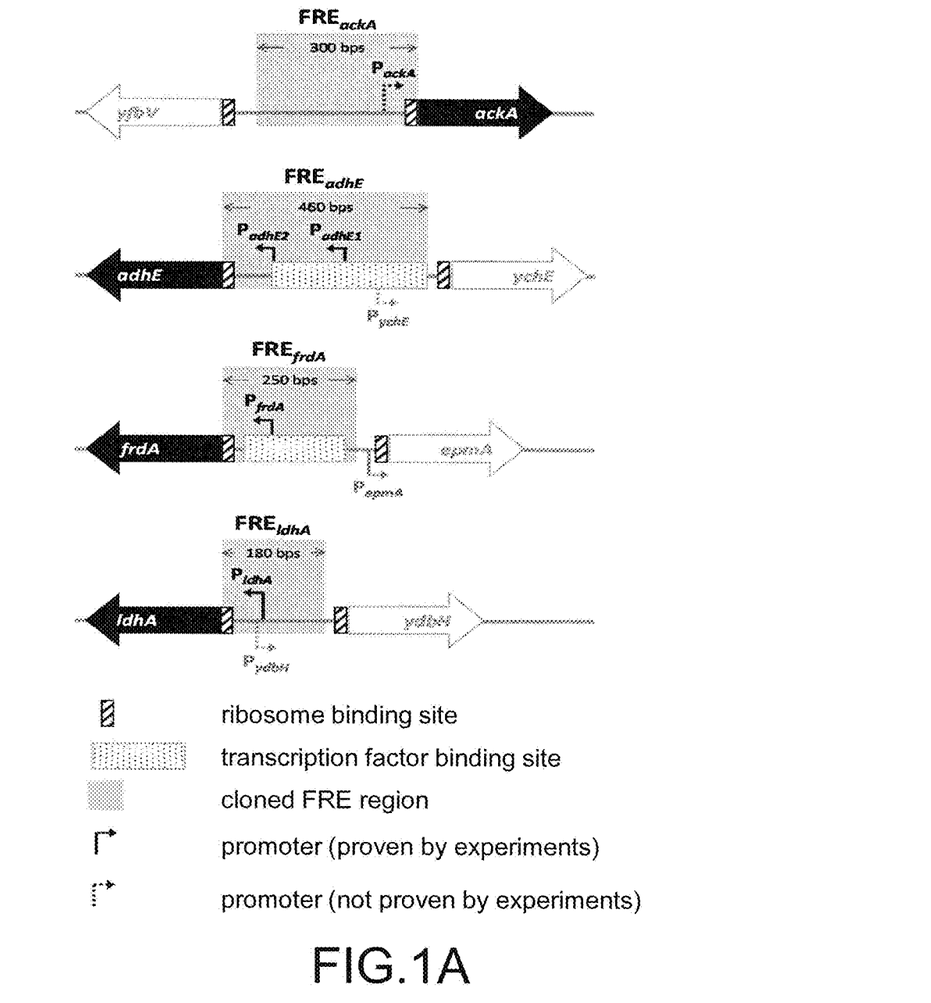
FIG. 1A is a schematic diagram of the fermentation regulatory element according to an embodiment of the invention.

FIG. 1A is a schematic diagram of the fermentation regulatory element according to an embodiment of the invention. Please referring to FIG. 1A, in an embodiment, the fermentation regulatory element includes a fermentation regulatory element of the ackA gene (referred to as $FRE_{ackA}$), a fermentation regulatory element of the adhE gene (referred to as $FRE_{adhE}$), a fermentation regulatory element of the frdA gene (referred to as $FRE_{frdA}$) or a fermentation regulatory element of the ldhA gene (referred to as $FRE_{ldhA}$). Specifically, the fermentation regulatory element used in the embodiment includes a promoter, a ribosome binding site and a transcription factor binding site of the ackA gene, the adhE gene, the frdA gene or the ldhA gene. Among the above, the fermentation regulatory element of the ackA gene ($FRE_{ackA}$) has, for example, a promoter $P_{ackA}$ and a sequence SEQ ID NO: 1 of 300 base pairs (bps), the fermentation regulatory element of the adhE gene ($FRE_{adhE}$) has, for example, a promoter $P_{adhE1}$, a promoter $P_{adhE2}$ and a sequence SEQ ID NO:2 of 460 base pairs (bps), the fermentation regulatory element of the frdA gene ($FRE_{frdA}$) has, for example, a promoter $P_{frdA}$ and a sequence SEQ ID NO:3 of 250 base pairs (bps), and the fermentation regulatory element of the ldhA gene ($FRE_{ldhA}$) has, for example, a promoter $P_{ldhA}$ and a sequence SEQ ID NO:4 of 180 base pairs (bps).

Then, please refer to FIG. 1A, for the clear illustration of the relative position of the fermentation regulatory element on the chromosome in an embodiment of the invention, it is particularly marked that the adjacent gene of the ackA gene is yfbV gene; the adjacent gene of the adhE gene is ychE gene and the adjacent promoter is $P_{ychE}$; the adjacent gene of the frdA gene is epmA gene and the adjacent promoter is $P_{epmA}$; the adjacent gene of the ldhA gene is ydbH gene and the adjacent promoter is $P_{ydbH}$.

Among the above, the butanol production related gene is not the fermentation gene or the gene of the upstream product of the fermentation in which the fermentation gene involves. In an embodiment, the butanol production related gene includes the gene of the product which is produced accompanied with the oxidation of NADH into $NAD^+$. That is, the fermentation gene and the butanol production related gene have consistent characteristics, in other words, both of them involve in the reaction which require NADH. Specifically, the butanol production related gene includes an atoB gene, an adhE2 gene, a crt gene, an hbd gene, a ter gene or an fdh gene.

In an embodiment of the invention, through cloning the butanol expression cassette in the expression vector, the recombinant plasmid configured to express the butanol production related gene is constructed.

In an embodiment, the expression vector includes, for example, an expression vector containing a ColE1 replication origin, an expression vector containing a Cola replication origin or an expression vector containing a pSC101 replication origin.

In an embodiment of the invention, the butanol production related gene expression method includes the following steps. First, the recombinant plasmid is transformed in a host cell, wherein the fermentation gene and the gene of the upstream product of the fermentation in which the fermentation gene involves have already been eliminated from the host cell. Then, the host cell is cultured under a fermentation condition, and the recombinant plasmid is induced to express the butanol production related gene.

In an embodiment, in the host cell, the gene of the reaction involving in the oxidation of NADH into $NAD^+$ or the reaction involving in the production of ATP has already been eliminated. In an embodiment, the eliminated gene is the fermentation gene or the gene of the upstream product of the fermentation in which the fermentation gene involves. "Gene of the upstream product" means that although not being the fermentation gene, it is the gene of the product in the fermentation route in which the fermentation gene involves. In an embodiment, the eliminated gene includes, for example, a pta gene, an adhE gene, an frdBC gene, or an ldhA gene.

In an embodiment of the invention, the step of culturing the host cell includes culturing the host cell to an early phase of a growth log phase or a late phase of the growth log phase under an aerobic environment, and transferring to an anaerobic environment for continuous culturing. Among the above, the recombinant plasmid is induced to express the butanol production related gene under an anaerobic environment, and no other addition of the inducer is needed.

Then, experiments are used to illustrate the construction of the recombinant plasmid and the butanol production related gene expression method using the recombinant plasmid, so as to describe the butanol production related gene expression platform constructed by the invention.

[Construction of the Recombinant Plasmid]

Figure 1B:
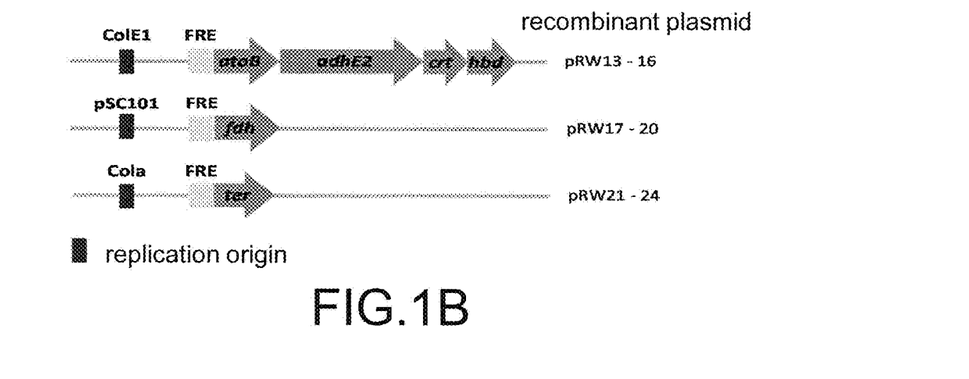
FIG. 1B is a schematic diagram of the combination of different recombinant plasmids according to an experimental example of the invention.

FIG. 1B is a schematic diagram of the combination of different recombinant plasmids according to an experimental example of the invention. Please refer to FIG. 1B, in the experimental example, the fermentation regulatory element $FRE_{ackA}$, $FRE_{adhE}$, $FRE_{frdA}$ or $FRE_{ldhA}$ is cloned in the expression vector containing the ColE1 replication origin, the expression vector containing the Cola replication origin or the expression vector containing the pSC101 replication origin, so that the fermentation regulatory element locates downstream of the ColE1 replication origin, downstream of the pSC101 replication origin or downstream of the Cola replication origin. In such a way, the expression vector containing the ColE1 replication origin can respectively include the fermentation regulatory element $FRE_{ackA}$, $FRE_{adhE}$, $FRE_{frdA}$ or $FRE_{ldhA}$, and therefore 4 kinds of expression vectors can be obtained. Similarly, 4 kinds of expression vectors can also be constructed through using the expression vector containing the pSC101 replication origin, and 4 kinds of expression vectors are constructed through using the expression vector containing Cola replication origin.

Then, please refer to FIG. 1B, the gene fragments including the atoB gene, the adhE2 gene, the crt gene and the hbd gene (that is, atoB-adhE2-crt-hbd) are sequentially cloned in 4 kinds of the above-mentioned expression vectors containing the ColE1 replication origin, so that the gene fragment locates downstream of the fermentation regulatory element, and the recombinant plasmid pRW13 and pRW16 as shown in table 1 are obtained.

Furthermore, please refer to FIG. 1B, the fdh gene is sequentially cloned in 4 kinds of the above-mentioned expression vectors containing the pSC101 replication origin, so that the fdh gene locates downstream of the fermentation regulatory element, and the recombinant plasmids pRW17 to pRW20 as shown in table 1 are obtained.

In addition, please refer to FIG. 1B, the ter gene is sequentially cloned in 4 kinds of the above-mentioned expression vectors containing the Cola replication origin, so that the ter gene locates downstream of the fermentation regulatory element, and the recombinant plasmids pRW21 to pRW24 as shown in table 1 are obtained.

In the recombinant plasmids pRW13~pRW24, the fermentation regulatory elements all locates upstream of the butanol production related gene, in such a way, the fermentation regulatory elements can control the expression of the butanol production related gene.

TABLE 1

| recombinant plasmid | gene type |
|---|---|
| pRW13 | $FRE_{ackA}$ :: atoB-adhE2-crt-hbd; ColE1 replication origin |
| pRW14 | $FRE_{adhE}$ :: atoB-adhE2-crt-hbd; ColE1 replication origin |
| pRW15 | $FRE_{frd}$ :: atoB-adhE2-crt-hbd; ColE1 replication origin |
| pRW16 | $FRE_{ldhA}$ :: atoB-adhE2-crt-hbd; ColE1 replication origin |
| pRW17 | $FRE_{ackA}$ :: fdh; pSC101 replication origin |
| pRW18 | $FRE_{adhE}$ :: fdh; pSC101 replication origin |
| pRW19 | $FRE_{frd}$ :: fdh; pSC101 replication origin |
| pRW20 | $FRE_{ldhA}$ :: fdh; pSC101 replication origin |
| pRW21 | $FRE_{ackA}$ :: ter; Cola replication origin |
| pRW22 | $FRE_{adhE}$ :: ter; Cola replication origin |
| pRW23 | $FRE_{frd}$ :: ter; Cola replication origin |
| pRW24 | $FRE_{ldhA}$ :: ter; Cola replication origin |

[The Better Recombinant Plasmid Combination is Chosen to Produce Butanol]

To express the atoB gene, the adhE2 gene, the crt gene, the hbd gene, the ter gene and the fdh gene simultaneously, one recombinant plasmid is chosen from 4 recombinant plasmids pRW13~pRW16 containing the ColE1 replication origin, so as to express the atoB-adhE2-crt-hbd gene; one recombinant plasmid is chosen from 4 recombinant plasmids pRW17~pRW20 containing the pSC101 replication origin, so as to express the fdh gene; and one recombinant plasmid is chosen from 4 recombinant plasmids pRW21~pRW24 containing the Cola replication origin, so as to express the ter gene. Therefore, there are 4×4×4=64 kinds of different recombinant plasmid combinations for the expression of butanol production related gene, so as to produce butanol.

Then, the host cell is provided, which is an *Escherichia coli* mutant in which the pta gene, adhE gene, frdBC gene and ldhA gene have already been eliminated. Then, one combination is chosen from the above-mentioned 64 kinds of recombinant plasmid combinations, and transformed to the *Escherichia coli* mutant.

Afterwards, the transformed *Escherichia coli* mutant is cultured under a fermentation condition. Specifically, the transformed *Escherichia coli* mutant is cultured to the stationary growth phase (that is, $OD_{600}$ is about 4) under the aerobic environment first, then transferred to the anaerobic environment for continuous culturing, and after 24 hours of the anaerobic environment culturing, the cell growth density and production amount of butanol are measured, and the result is shown in FIG. 2.

Figure 2:
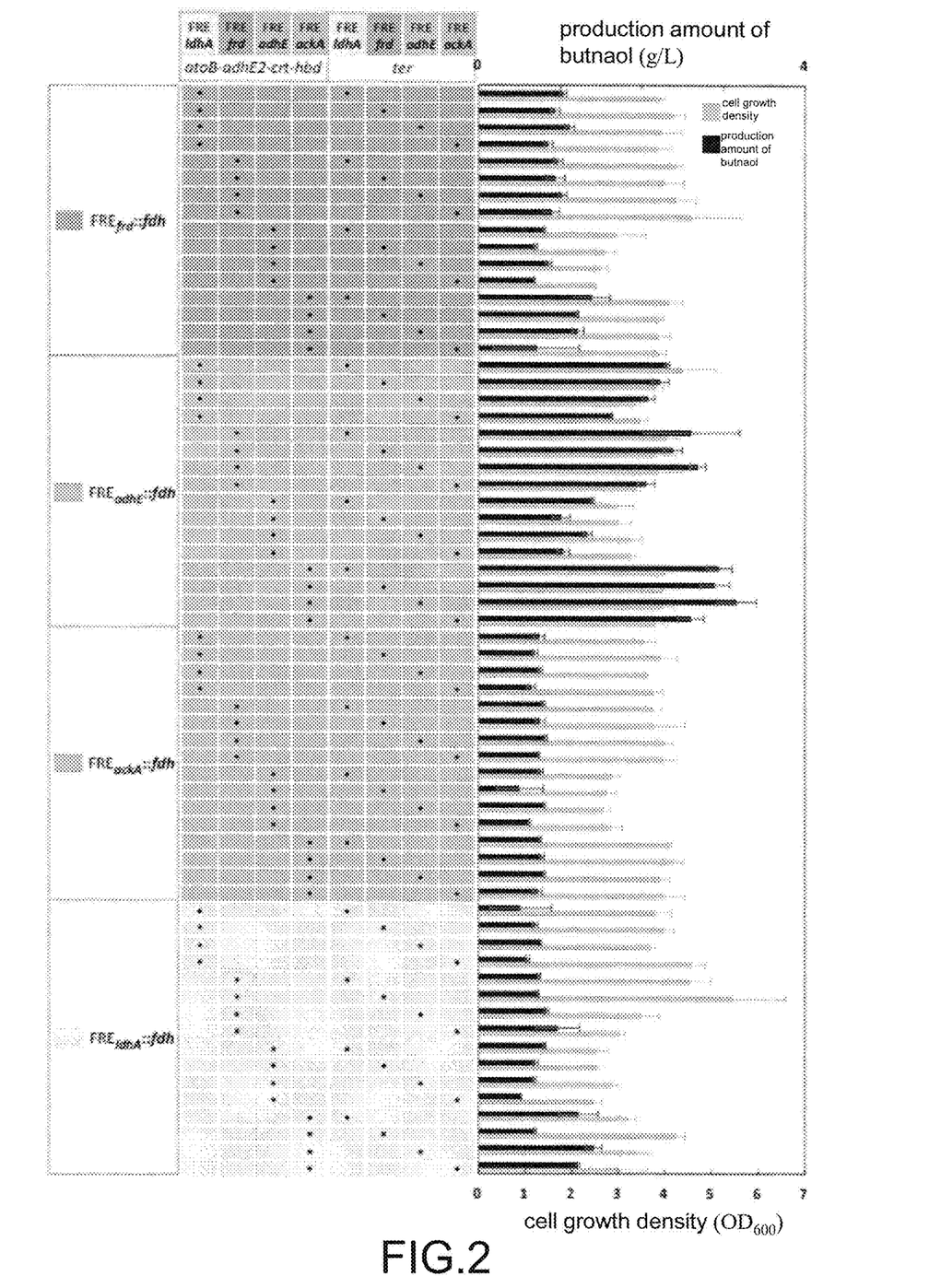
FIG. 2 is a relation diagram of the combination of different recombinant plasmids versus cell growth density and production amount of butanol according to an experimental example of the invention.

It can be known from FIG. 2 that, the recombinant plasmid combination having better production amount of butanol is $FRE_{ac}kA$::atoB-adhE2-crt-hbd+$FRE_{adhE}$::fdh+

FRE$_{adhE}$::ter. That is, the *Escherichia coli* mutant (hereinafter referred to as recombinant *Escherichia coli* mutant) containing the recombinant plasmid FRE$_{ackA}$::atoB-adhE2-crt-hbd, FRE$_{adhE}$::fdh and the FRE$_{adhE}$::ter can produce more butanol.

Then, the *Escherichia coli* mutant with the above-mentioned recombinant plasmid combination (FRE$_{ackA}$::atoB-adhE2-crt-hbd+FRE$_{adhE}$::fdh+FRE$_{adhE}$::ter) transformed therein is cultured under following condition respectively, so as to find out the best production condition of butanol.

[Effect of the Oxygen Supply Condition and Culture Vessel on the Production Amount of Butanol]

Experimental Example 1

Under the aerobic environment, the above-mentioned recombinant *Escherichia coli* mutant is cultured to the growth log phase in the TB (Terrific Broth) culture medium containing antibiotics, then transferred to flask for continuous culturing under the aerobic environment. After 24 hours of culturing, the cell growth density and production amount of butanol are measured.

Experimental Example 2

The method similar to the experimental example 1 is used to culture the recombinant *Escherichia coli* mutant, and the difference lies in that the tube is used to replace the flask as a culture vessel, and the micro-aerobic environment is used to replace the aerobic environment as a condition for continuous culturing.

Experimental Example 3

The method similar to the experimental example 1 is used to culture the recombinant *Escherichia coli* mutant, and the difference lies in that the micro-aerobic environment is used to replace the aerobic environment as a condition for continuous culturing.

Experimental Example 4

The method similar to the experimental example 2 is used to culture the recombinant *Escherichia coli* mutant, and the difference lies in that the anaerobic environment is used to replace the aerobic environment as a condition for continuous culturing.

Figure 3:
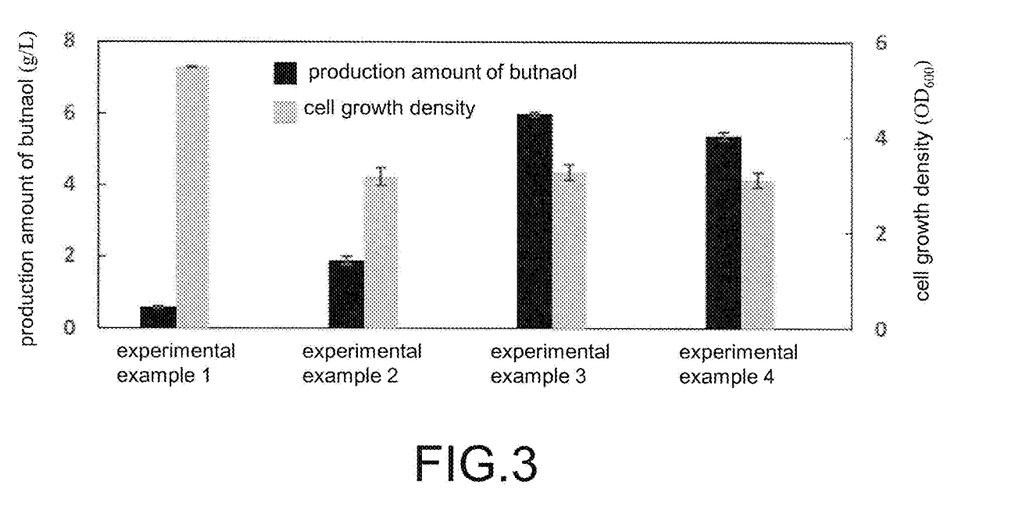
FIG. 3 is a relation diagram of the oxygen supply condition and culture vessel versus cell growth density and production amount of butanol according to experimental example 1 to experimental example 4.

FIG. 3 is a relation diagram of the oxygen supply condition and culture vessel versus cell growth density and production amount of butanol according to experimental example 1 to experimental example 4. Please refer to FIG. 3, the production amount of butanol under the micro-aerobic environment (experimental example 3) and the anaerobic environment (experimental example 4, in which the production amount of butanol is 5.4 g/L) are similar to each other, but the production amount of butanol under the aerobic environment (experimental example 1) is significantly reduced to 0.6 g/L. In addition, compared to the production amount of butanol using flask as culture vessel and cultured under the micro-aerobic environment (experimental example 3), the production amount of butanol using tube as culture vessel and cultured under the micro-aerobic environment (experimental example 2) is only 2 g/L. That is, the fermentation regulatory element in the recombinant plasmid can be induced under the anaerobic environment or the micro-aerobic environment in which the oxygen is not completely removed, so as to express the butanol production related gene.

[Effect of the Culture Medium on the Production Amount of Butanol]

Experimental Example 5

Under the aerobic environment, the recombinant *Escherichia coli* mutant is cultured to the medium phase of the growth log phase in the TB culture medium containing antibiotics, then transferred to tube for continuous culturing under the anaerobic environment. After 24 hours of culturing, the cell growth density and production amount of butanol are measured.

Experimental Example 6

The method similar to the experimental example 5 is used to culture the recombinant *Escherichia coli* mutant, and the difference lies in that the M9 culture medium containing 0.5% yeast extract is used to replace the TB culture medium. Among the above, compared to the rich nutrients required for the cell growth provided by the yeast extract, the M9 culture medium only contain the minimum nutrients required for the cell growth.

Experimental Example 7

The method similar to the experimental example 5 is used to culture the recombinant *Escherichia coli* mutant, and the difference lies in that the M9 culture medium is used to replace the TB culture medium.

Figure 4:
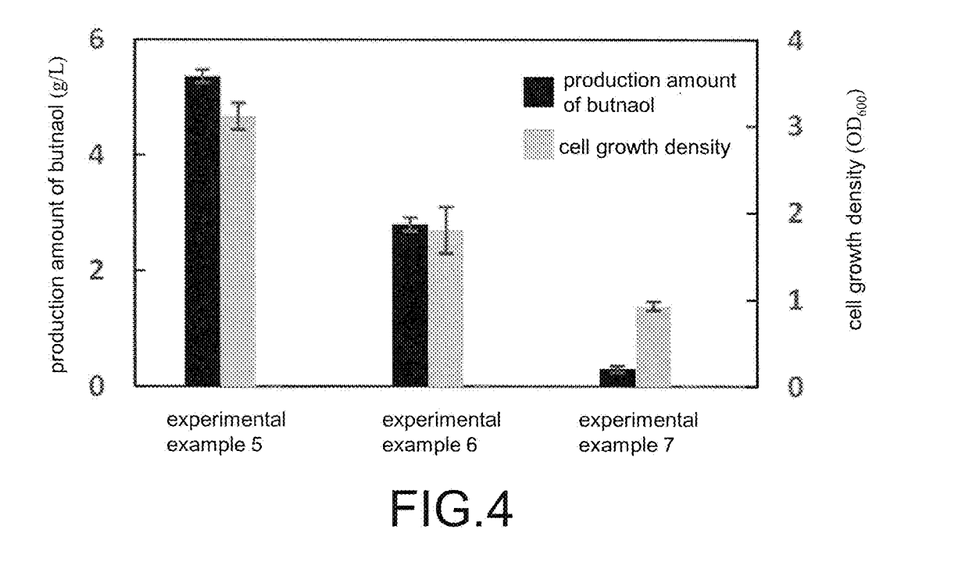
FIG. 4 is a relation diagram of the culture medium versus cell growth density and production amount of butanol according to experimental example 5 to experimental example 7.

FIG. 4 is a relation diagram of the culture medium versus cell growth density and production amount of butanol according to experimental example 5 to experimental example 7. Please refer to FIG. 4, compared to the production amount of butanol using the TB culture medium (experimental example 5), the production amount of butanol using the M9 culture medium using 0.5% yeast extract (experimental example 6) is reduced by about 50%, and the production amount of butanol using the M9 culture medium (experimental example 7) is further reduced by about 95%. In other words, in order to make the recombinant *Escherichia coli* mutant effectively produce butanol under the anaerobic environment, rich nutrients such as the yeast extract or tryptone may be necessary.

[Effect of the Timing of Transferring to the Anaerobic Environment on the Production of Butanol]

Experimental Example 8

Under the aerobic environment, the recombinant *Escherichia coli* mutant is cultured to growth retardation phase (OD$_{600}$ is about 0.03) in the TB culture medium containing antibiotics, and transferred to the tube for continuous culturing under the anaerobic environment, the pH value is adjusted to 6.8 to 7.2 every 8 to 24 hours, and the glucose concentration is adjusted to 20 g/L or more. After 72 hours of culturing, the cell growth density and production amount of butanol are measured.

Experimental Example 9

The method similar to the experimental example 8 is used to culture the recombinant *Escherichia coli* mutant, the difference lies only in the timing of transferring to the anaerobic environment, and the growth log phase (that is, $OD_{600}$ is about 0.4) is used to replace the growth retardation phase (that is, $OD_{600}$ is about 0.03).

Experimental Example 10

The method similar to the experimental example 8 is used to culture the recombinant *Escherichia coli* mutant, the difference lies only in the timing of transferring to the anaerobic environment, and the early phase of the growth stationary phase (that is, $OD_{600}$ is about 2) is used to replace the growth retardation phase (that is, $OD_{600}$ is about 0.03).

Experimental Example 11

The method similar to the experimental example 8 is used to culture the recombinant *Escherichia coli* mutant, the difference lies only in the timing of transferring to the anaerobic environment, and the late phase of the growth stationary phase (that is, $OD_{600}$ is about 9) is used to replace the growth retardation phase (that is, $OD_{600}$ is about 0.03).

Experimental Example 12

Under the anaerobic environment, the recombinant *Escherichia coli* mutant is cultured for 16~18 hours in the TB culture medium containing antibiotics, and the cell growth density is concentrated to $OD_{600}$ being about 9, then transferred to tube for continuous culturing under the anaerobic environment. Among the above, the pH value is adjusted to 6.8 to 7.2 every 8 to 24 hours, and the glucose concentration is adjusted to 20 g/L or more. After 72 hours of culturing, the cell growth density and production amount of butanol are measured.

That is, the experimental example 12 uses the method similar to the experimental example 11 for the culturing of recombinant *Escherichia coli* mutant, the difference lies in that before the transferring to tube for the culturing, "after the cells are cultured for 16~18 hours under the anaerobic environment, then the cell growth density is concentrated to $OD_{600}$ being about 9" is used to replace "the cells is cultured to the late phase of the growth stationary phase under the aerobic environment ($OD_{600}$ is about 9)".

Figure 5A:
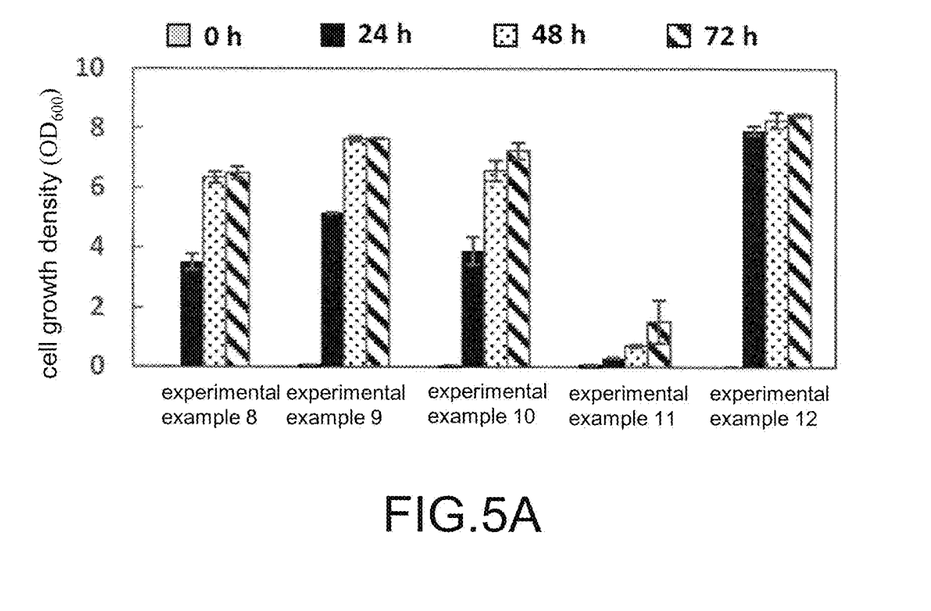
FIG. 5A is a relation diagram of the timing of transferring to an anaerobic environment versus cell growth density according to experimental example 8 to experimental example 12.
Figure 5B:
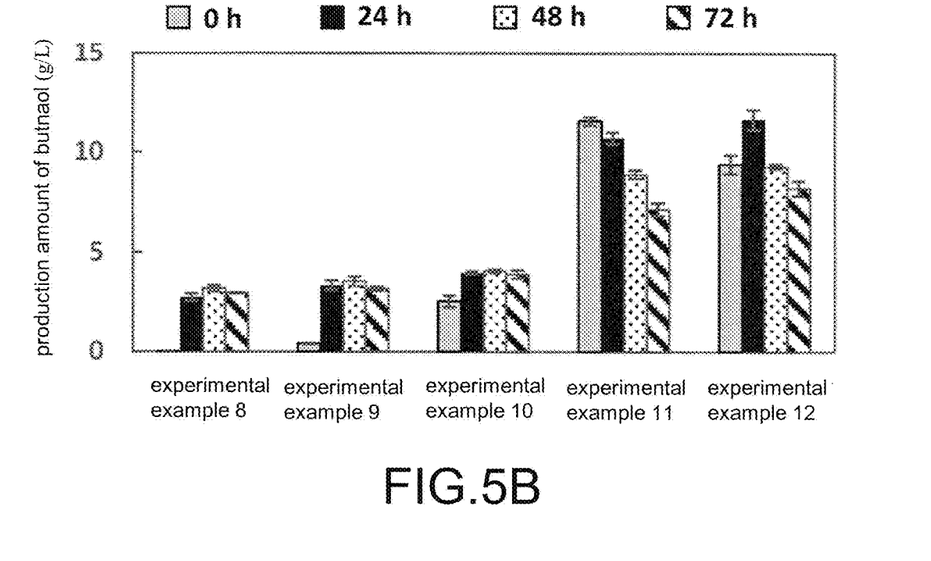
FIG. 5B is a relation diagram of the timing of transferring to an anaerobic environment versus production amount of butanol according to experimental example 8 to experimental example 12.

FIGS. 5A and 5B are relation diagrams of the timing of transferring to an anaerobic environment versus cell growth density and production amount of butanol according to experimental example 8 to experimental example 12 respectively. Please refer to FIG. 5A, culturing to the growth retardation phase (experimental example 8), culturing to the growth log phase (experimental example 9) or culturing to the early phase of growth stationary phase (experimental example 10), and then being transferred to the anaerobic environment for continuous culturing can all induce the recombinant plasmid to express the gene, and similar production amount of butanol can be obtained (about 6~8 g/L). However, the obtained production amount of butanol by culturing to the late phase of the stationary phase (experimental example 11) and then transferred to the anaerobic environment for continuous culturing is significantly reduced.

Please refer to FIG. 5B, compared to culturing to the late phase of stationary phase under the aerobic environment, and then transferred to the anaerobic environment for the expression of butanol production related gene in the experimental example 11, the butanol production related gene is expressed under the anaerobic environment at the beginning of the growth in experimental example 12. Therefore, the production amount of butanol can approximately reach 10 g/L after the concentrating and continuous culturing for 24 hours in experimental example 12.

[Effect of Antibiotics on the Production of Butanol]

Experimental Example 13

Under the aerobic environment, the recombinant *Escherichia coli* mutant is cultured to the growth log phase ($OD_{600}$ is about 0.4) in the TB culture medium containing antibiotics, and then transferred to tube for continuous culturing under the anaerobic environment, wherein the TB culture medium in use contains no antibiotics. The cell growth density and the production amount of butanol are measured every 12 hours of culturing, and the pH value is adjusted to 6.8 to 7.2 and the glucose concentration is adjusted to 20 g/L or more.

Experimental Example 14

Under the anaerobic environment, the recombinant *Escherichia coli* mutant is cultured for 16~18 hours in the TB culture medium including no antibiotics, and then the cell growth density is concentrated to $OD_{600}$ being about 9. After that, the cells are transferred to tube for continuous culturing under the anaerobic environment, wherein the culture medium also includes no antibiotics. The cell growth density and the production amount of butanol are measured every 24 hours of culturing, and the pH value is adjusted to 6.8 to 7.2 and the glucose concentration is adjusted to 20 g/L or more.

Figure 6A:
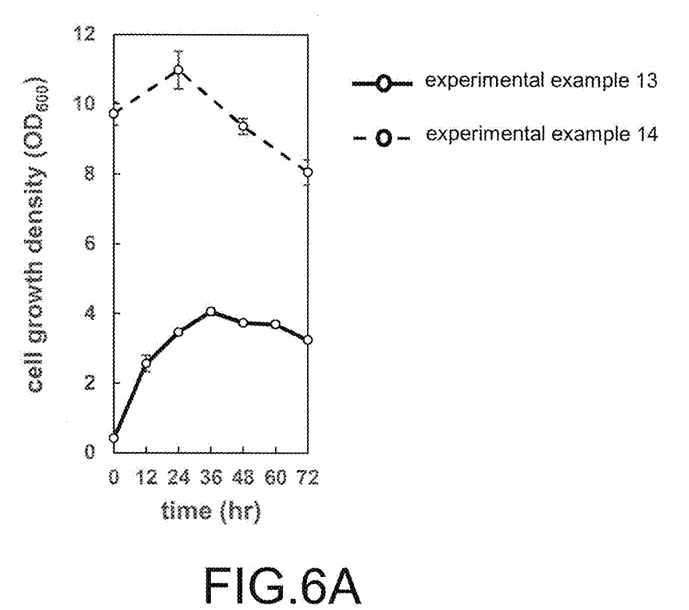
FIG. 6A is a relation diagram of the antibiotics versus cell growth density according to experimental example 13 and experimental example 14.
Figure 6B:
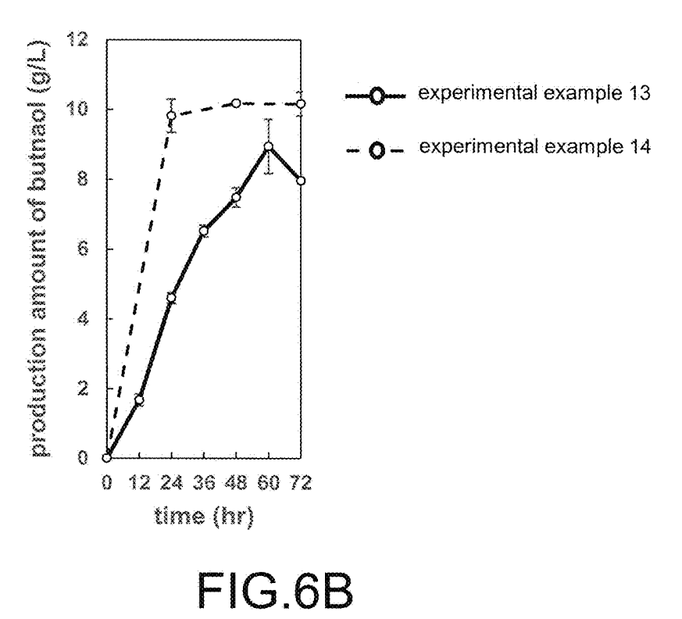
FIG. 6B is a relation diagram of the antibiotics versus production amount of butanol according to experimental example 13 and experimental example 14.

FIG. 6A to FIG. 6B are relation diagrams of the antibiotics versus cell growth density and production amount of butanol according to experimental example 13 and experimental example 14 respectively. Please refer to FIG. 6A and FIG. 6B, compared to continuously using the TB culture medium containing the antibiotics after the transferring to the anaerobic environment in the experimental example 9, the TB culture medium including no antibiotics is used instead after transferring to the anaerobic environment in experimental example 14. It can be known from the result that the culture method using the TB culture medium including no antibiotics under the anaerobic environment causes no significant change on the cell growth density and production amount of butanol.

Please refer to FIG. 6A and FIG. 6B, compared to using the TB culture medium containing the antibiotics in the experimental example 12, the TB culture medium including no antibiotics is used in experimental example 14. It can be known from the result that the culture method using the TB culture medium including no antibiotics under the anaerobic environment causes no significant change on the cell growth density and production amount of butanol.

In other words, under the anaerobic environment, when the TB culture medium including no antibiotics is used for the culturing of the recombinant *Escherichia coli* mutant, the recombinant plasmid won't be excluded by the recombinant *Escherichia coli* mutant, instead, it still exists in the recombinant *Escherichia coli* mutant, so as to express the gene consistently and produce butanol.

Based on the above, the butanol expression cassette provided by the invention includes a fermentation regulatory element and a butanol production related gene, wherein the fermentation regulatory element can, for example, induce the expression of the butanol production related gene under the anaerobic environment or micro-aerobic environment. That is, through the controlling of the fermentation regulatory element by the host cell itself, no addition of the inducer is needed for the expression of the butanol production related gene. In addition, in order to grow under the anaerobic environment, the host cell must keep the recombinant plasmid containing the fermentation regulatory element therein. With such property, in the invention, the host cell is prevented from excluding the recombinant plasmid without the addition of antibiotics or inducers, so that the host cell can continuously express the butanol production related gene. In other words, with the use of the recombinant plasmid constructed by the butanol expression cassette containing the fermentation regulatory element of the invention, the butanol production related gene can be expressed under the condition without the addition of inducer or antibiotics additionally, therefore, a production platform able to achieve self-regulation is provided. In such a way, the product quality can be significantly increased or the production cost can be reduced with the application of the production platform.

It will be apparent to those skilled in the art that various modifications and variations can be made to the disclosed embodiments without departing from the scope or spirit of the invention. In view of the foregoing, it is intended that the invention covers modifications and variations provided that they fall within the scope of the following claims and their equivalents.

What is claimed is:

1. A butanol expression cassette, comprising:
a butanol production related gene; and
a fermentation related gene regulatory element (FRE), configured to control an expression of the butanol production related gene and located upstream of the butanol production related gene, wherein the fermentation related gene regulatory element comprises a promoter, a ribosome binding site and a transcription factor binding site of a fermentation related gene,
wherein a fermentation in which the fermentation related gene regulatory element involves comprises an acetic acid fermentation, an alcohol fermentation, a succinic acid fermentation or a lactic acid fermentation, and the butanol production related gene is not the fermentation related gene or a gene of an upstream product of the fermentation in which the fermentation related gene involves, wherein the fermentation related gene comprises an ackA (acetate kinase) gene, an adhE (aldehyde-alcohol dehydrogenase) gene, an frdA (fumarate reductase flavoprotein subunit) gene or an ldhA (L-lactate dehydrogenase A chain) gene, when the fermentation related gene is the ackA gene, the fermentation related gene regulatory element comprising a nucleotide sequence of SEQ ID NO:1, when the fermentation related gene is the adhE gene, the fermentation related gene regulatory element comprising a nucleotide sequence of SEQ ID NO:2, when the fermentation related gene is the frdA gene, the fermentation related gene regulatory element comprising a nucleotide sequence of SEQ ID NO:3, and when the fermentation related gene is the ldhA gene, the fermentation related gene regulatory element comprising a nucleotide sequence of SEQ ID NO:4,
the butanol production related gene is expressed under the condition without the addition of inducer or antibiotics.

2. The butanol expression cassette according to claim 1, wherein the butanol production related gene comprises an atoB (acetyl-CoA acetyl transferase) gene, an adhE2 (aldehyde-alcohol dehydrogenase) gene, a crt (crotonase) gene, an hbd (3-hydroxybutyryl-CoA dehydrogenase) gene, a ter (trans-enoyl-CoA reductase) gene or an fdh (formaldehyde dehydrogenase) gene.

3. A recombinant plasmid configured to express a butanol production related gene, comprising:
an expression vector; and
the butanol expression cassette according to claim 1, cloned in the expression vector.

4. The recombinant plasmid according to claim 3, wherein the expression vector comprises an expression vector containing a ColE1 replication origin, an expression vector containing a Cola replication origin or an expression vector containing a pSC101 replication origin.

5. A butanol production related gene expression method, comprising:
transforming the recombinant plasmid according to claim 3 in a host cell, wherein a pta (phosphate acetyltransferase) gene, an adhE gene, an frdBC gene and an ldhA gene have been eliminated from the host cell;
culturing the host cell under a fermentation condition; and
inducing the recombinant plasmid to express the butanol production related gene.

6. The method according to claim 5, wherein a method of inducing the recombinant plasmid is cultured in an anaerobic environment.

7. The method according to claim 5, wherein a step of culturing the host cell comprises:
under an aerobic environment, culturing the host cell to an early phase of a growth log phase or a late phase of the growth log phase; and
transferring to an anaerobic environment for continuous culturing.

8. The method according to claim 7, wherein in the anaerobic environment, a pH value is adjusted to 6.8 to 7.2 every 8 to 24 hours, and a glucose concentration is adjusted to 20 g/L or more.

9. The method according to claim 5, wherein the host cell comprises an *Escherichia coli*.

\* \* \* \* \*

SEQUENCE LISTING

<160> NUMBER OF SEQ ID NOS: 4

<210> SEQ ID NO 1
<211> LENGTH: 300
<212> TYPE: DNA
<213> ORGANISM: Escherichia coli

<400> SEQUENCE: 1

```
tgtgcaaatt cacaactcag cgggacaacg ttcaaaacat tttgtcttcc atacccacta      60
tcaggtatcc tttagcagcc tgaaggccta agtagtacat attcattgag tcgtcaaatt     120
catatacatt atgccattgg ctgaaaatta cgcaaaatgg catagactca agatatttct     180
tccatcatgc aaaaaaaatt tgcagtgcat gatgttaatc ataaatgtcg gtgtcatcat     240
gcgctacgct ctatggctcc ctgacgtttt tttagccacg tatcaattat aggtacttcc     300
```

<210> SEQ ID NO 2
<211> LENGTH: 460
<212> TYPE: DNA
<213> ORGANISM: Escherichia coli

<400> SEQUENCE: 2

```
aaagccggat aatgttagcc ataaataagg ttgaaaagac gcgctgacaa tacgcctttt      60
gacagcattt ttcacctcct aactacttaa aattgctatc attcgttatt gttatctagt     120
tgtgcaaaac atgctaatgt agccaccaaa tcatactaca atttattaac tgttagctat     180
aatggcgaaa agcgatgctg aaaggtgtca gctttgcaaa aatttgattt ggatcacgta     240
atcagtaccc agaagtgagt aatcttgctt acgccacctg gaagtgacgc attagagata     300
ataactctaa tgtttaaact cttttagtaa atcacagtga gtgtgagcgc gagtaagctt     360
ttgattttca taggttaagc aaatcatcac cgcactgact atactctcgt attcgagcag     420
atgatttact aaaaagttt aacattatca ggagagcatt                            460
```

<210> SEQ ID NO 3
<211> LENGTH: 250
<212> TYPE: DNA
<213> ORGANISM: Escherichia coli

<400> SEQUENCE: 3

```
atcaaacagc ggtgggcagt gactaaaaaa agcacgatct gatggtttag taattaaatt      60
aatcatcttc agtgataatt tagccctctt gcgcactaaa aaaatcgatc tcgtcaaatt     120
tcagacttat ccatcagact atactgttgt acctataaag gagcagtgga atagcgttcg     180
cagaccgtaa ctttcaggta cttaccctga agtacgtggc tgtgggataa aaacaatctg     240
gaggaatgtc                                                            250
```

```
<210> SEQ ID NO 4
<211> LENGTH: 180
<212> TYPE: DNA
<213> ORGANISM: Escherichia coli

<400> SEQUENCE: 4
aaattaagca ttcaatacgg gtattgtggc atgtttaacc gttcagttga aggttgcgcc        60
tacactaagc atagttgttg atgaattttt caatatcgcc atagctttca attaaatttg       120
aaattttgta aaatattttt agtagcttaa atgtgattca acatcactgg agaaagtctt       180
```